(12) United States Patent
Yu et al.

(10) Patent No.: US 8,555,710 B2
(45) Date of Patent: Oct. 15, 2013

(54) SYSTEMS AND METHODS FOR ANALYZING LIQUIDS UNDER VACUUM

(75) Inventors: Xiao-Ying Yu, Richland, WA (US); Li Yang, Richland, WA (US); James P. Cowin, Richland, WA (US); Martin J. Iedema, Richland, WA (US); Zihua Zhu, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 399 days.

(21) Appl. No.: 13/047,025

(22) Filed: Mar. 14, 2011

(65) Prior Publication Data

US 2012/0234082 A1 Sep. 20, 2012

(51) Int. Cl.
*G01N 1/00* (2006.01)
*G01F 23/00* (2006.01)

(52) U.S. Cl.
USPC .................................. 73/64.56; 250/440.11

(58) Field of Classification Search
USPC ........ 73/61.41, 64.55, 64.56, 865.6; 250/428, 250/430, 435, 438, 440.11; 356/436, 440; 850/9, 12, 14, 15
See application file for complete search history.

(56) References Cited

U.S. PATENT DOCUMENTS

| | | | |
|---|---|---|---|
| 8,059,271 B2 | 11/2011 | Marsh et al. | |
| 8,102,523 B1 | 1/2012 | Marsh et al. | |
| 2007/0145287 A1* | 6/2007 | Chao et al. | 250/440.11 |
| 2009/0294702 A1* | 12/2009 | Imanishi et al. | 250/576 |
| 2009/0323069 A1* | 12/2009 | Naessens et al. | 356/440 |
| 2010/0193398 A1* | 8/2010 | Marsh et al. | 206/710 |
| 2012/0017415 A1 | 1/2012 | Marsh et al. | |

OTHER PUBLICATIONS

Lee, Jeonghoon, et al., "Development of an Automated Digestion and Droplet Deposition Microfluidic Chip for MALDI-TOF MS," Journal of Am Soc Mass Spectrom, 2008, 964-972 pages, vol. 19, Baton Rouge, LA, USA.

Onnerfjord, Patrik, et al., "Homogeneous Sample Preparation for Automated High Throughput Analysis with Matrix-Assisted Laser Desorption/Ionisation Time-of-flight Mass Spectrometry," Rapid Communications in Mass Spectrometry, 1999, 315-322 pages, vol. 13, Lund, Sweden.

Liu, Jun, et al., "Electrophoresis Separation in Open Microchannels. A Method for Coupling Electrophoresis with MALDI-MS," Analytical Chemistry, 2001, 2147-2151 pages, vol. 73, Davis, California, USA.

(Continued)

*Primary Examiner* — Hezron E Williams
*Assistant Examiner* — Nathaniel Kolb
(74) *Attorney, Agent, or Firm* — Allan C. Tuan (57) ABSTRACT

Systems and methods for supporting a liquid against a vacuum pressure in a chamber can enable analysis of the liquid surface using vacuum-based chemical analysis instruments. No electrical or fluid connections are required to pass through the chamber walls. The systems can include a reservoir, a pump, and a liquid flow path. The reservoir contains a liquid-phase sample. The pump drives flow of the sample from the reservoir, through the liquid flow path, and back to the reservoir. The flow of the sample is not substantially driven by a differential between pressures inside and outside of the liquid flow path.

An aperture in the liquid flow path exposes a stable portion of the liquid-phase sample to the vacuum pressure within the chamber. The radius, or size, of the aperture is less than or equal to a critical value required to support a meniscus of the liquid-phase sample by surface tension.

19 Claims, 7 Drawing Sheets

(56) References Cited

OTHER PUBLICATIONS

Preisler, Jan, et al., "On-Line MALDI-TOF MS Using a Continuous Vacuum Deposition Interface," Analytical Chemistry, Dec. 15, 1998, 5278-5287 pages, vol. 70, No. 24, Boston, MA, USA.

Murray, Kermit K., et al., "Liquid Sample Introduction for Matrix-Assisted Laser Desorption Ionization," Analytical Chemistry, Sep. 15, 1993, 2534-2537 pages, vol. 65, No. 18, College Station, TX, USA.

Orsnes, Henrick, et al., "A Rotating Ball Inlet for On-Line MALDI Mass Spectrometry," Analytical Chemistry, Jan. 1, 2000, 251-254 pages, vol. 72, No. 1, Atlanta, GA, USA.

Zhang, Xia, et al., "On-Line Single Droplet Deposition for MALDI Mass Spectrometry," Analytical Chemistry, Jan. 1, 2000, 251-254 pages, vol. 72, No. 1, Atlanta, GA, USA.

Hirschberg, Daniel, et al., "Identification of Endothelial Proteins by MALDI-MS Using a Compact Disc Microfluidic System," The Protein Journal, May 2004, 263-271 pages, vol. 23, No. 4.

* cited by examiner

SYSTEMS AND METHODS FOR ANALYZING LIQUIDS UNDER VACUUM

STATEMENT REGARDING FEDERALLY SPONSORED RESEARCH OR DEVELOPMENT

This invention was made with Government support under Contract DE-AC0576RL01830 awarded by the U.S. Department of Energy. The Government has certain rights in the invention.

BACKGROUND

Chemical analysis of liquids under vacuum, especially at surface regions and at liquid interfaces, can yield valuable data and information that might provide insight into environmental and biological systems. However, many of the instruments for analysis of surfaces and interfaces are vacuum based, and are not compatible with the high vapor pressure associated with liquid-phase samples. While some approaches exist for investigating liquids, many involve jets that put a large (sometimes overwhelming) load on vacuum pumps and/or significant cooling that limits the kinds of available analyses. Accordingly, methods and systems are needed for analyzing liquids under vacuum.

SUMMARY

The present invention includes systems and methods for supporting a liquid against a vacuum pressure in a chamber to enable analysis of the liquid surface using vacuum-based chemical analysis instruments. No electrical or fluid connections are required to pass through the chamber walls, making embodiments of the present invention substantially self-contained. Vacuum pressures within the chamber are typically less than or equal to approximately $5 \times 10^{-6}$ Torr.

The systems of the present invention can comprise a reservoir, a pump, and a liquid flow path. The reservoir contains a liquid-phase sample. Exemplary samples can comprise aqueous or organic solutions. The pump drives flow of the sample from the reservoir, through the liquid flow path, and back to the reservoir. The flow of the sample is not substantially driven by a differential between pressures inside and outside of the liquid flow path. An example of a pump includes, but is not limited to, an electro-osmotic pump.

An aperture in the liquid flow path exposes a stable portion of the liquid-phase sample to the vacuum pressure within the chamber. The radius, or size, of the aperture is less than or equal to a critical value required to support a meniscus of the liquid-phase sample by surface tension against the vacuum pressure within the chamber. Embodiments of the present invention do not generate a jet or spray out of the aperture. Rather, the aperture size, sample surface tension, liquid flow parameters, and chamber pressure are maintained to establish a stable liquid-vacuum interface.

While the liquid flow path can have a diameter that is less than approximately 1 mm, in preferred embodiments, the diameter is less than 500 micrometers. In particular, the liquid flow path preferably has a diameter of less than 50 micrometers. Depending on the properties of the liquid-phase sample, the surfaces of the liquid flow path and/or the aperture can comprise a treatment altering the hydrophilicity in order to facilitate establishment of a stable liquid-vacuum interface at the aperture.

The system can further comprise a gas doser directing a gas to a region proximal to the aperture. The gas can locally alter the partial pressure near the aperture, helping to minimize evaporation and/or increase stability of the liquid-phase sample. Alternatively, or in addition, the gas can comprise a first reactant that can react with a second reactant in the liquid-phase sample. The reaction can, therefore, be studied in-situ.

In some embodiments, the system can further comprise at least one vacuum-based chemical analysis instrument to analyze the liquid-phase sample surface region. As used herein, vacuum-based chemical analysis instruments refer to techniques and devices that require relatively large mean free path lengths between molecules and fragments, which path lengths are associated with vacuum pressures. The analyses typically, though not always, involve directing a beam of ions, electrons, or ionizing radiation (e.g., X-rays) at the liquid surface and detecting the emitted ions, neutrals, electrons, and/or photons. Examples of vacuum-based chemical analysis instruments can include, but are not limited to, X-ray photoelectron spectroscopy (XPS), scanning electron microscopy (SEM), secondary ion mass spectrometry (SIMS), helium ion microscopy (HeIM), Auger electron spectroscopy (AES), Rutherford backscattering spectrometry (RBS), and transmission electron microscopy (TEM).

In a particular embodiment, a system for analyzing a liquid surface under vacuum comprises a reservoir, a pump, and a liquid flow path, and is characterized by a lack of electrical and fluid connections passing through walls of a chamber in which the system is emplaced. During operation, the chamber can have a vacuum pressure less than or equal to approximately $5 \times 10^{-6}$ Torr. The reservoir contains a liquid-phase sample comprising an aqueous or organic solution. The pump drives flow of the sample from the reservoir, through the liquid flow path, and back to the reservoir, wherein at least a portion of the liquid flow path has a diameter less than 50 micrometers and the flow is not substantially driven by a differential between pressures inside and outside of the liquid flow path. An aperture in the liquid flow path exposes a stable surface of the liquid-phase sample to the vacuum pressure within the chamber. The aperture has a size, or radius, less than or equal to a critical value required to support a meniscus of the liquid-phase sample by surface tension against the vacuum pressure within the chamber. The system further comprises at least one vacuum-based chemical analysis installment to analyze the liquid-phase sample surface region through the aperture.

Embodiments of the present invention also include methods for analyzing liquid surfaces under vacuum. The methods can comprise emplacing a system comprising a reservoir, a pump, and a liquid flow path, in a chamber having a vacuum pressure. The system lacks electrical and fluid connections that pass through walls of the chamber. The methods further comprise driving flow of liquid-phase sample from the reservoir, through the liquid flow path, and back to the reservoir, and exposing a stable surface of the liquid-phase sample through an aperture in the liquid flow path to the vacuum pressure within the chamber. The driving of the flow is not substantially provided by a differential between pressures inside and outside of the liquid flow path. The aperture has a radius less than or equal to a critical value required to support a meniscus of the liquid-phase sample by surface tension against the vacuum pressure within the chamber. Finally, the methods comprise analyzing the liquid-phase sample surface region through the aperture by at least one vacuum-based chemical analysis instrument.

In some embodiments, the methods can further comprise directing a gas through a gas doser to a region proximal to the aperture. The gas can locally alter the partial pressure in the region near the aperture, helping to decrease evaporation and/or increase stability of the liquid-phase sample. Alternatively, or in addition, the methods can comprise reacting a first reactant in the gas with a second reactant in the liquid-phase sample.

The purpose of the foregoing abstract is to enable the United States Patent and Trademark Office and the public generally, especially the scientists, engineers, and practitioners in the art who are not familiar with patent or legal terms or phraseology, to determine quickly from a cursory inspection the nature and essence of the technical disclosure of the application. The abstract is neither intended to define the invention the application, which is measured by the claims, nor is it intended to be limiting as to the scope of the invention in any way.

Various advantages and novel features of the present invention are described herein and will become further readily apparent to those skilled in this art from the following detailed description. In the preceding and following descriptions, the various embodiments, including the preferred embodiments, have been shown and described. Included herein is a description of the best mode contemplated for carrying out the invention. As will be realized, the invention is capable of modification in various respects without departing from the invention. Accordingly, the drawings and description of the preferred embodiments set forth hereafter are to be regarded as illustrative in nature, and not as restrictive.

DESCRIPTION OF DRAWINGS

Embodiments of the invention are described below with reference to the following accompanying drawings.

FIG. 5a-5e includes TOFSIMS images of an aperture according to embodiments of the present invention.

DETAILED DESCRIPTION

The following description includes the preferred best mode of one embodiment of the present invention. It will be clear from this description of the invention that the invention is not limited to these illustrated embodiments but that the invention also includes a variety of modifications and embodiments thereto. Therefore the present description should be seen as illustrative and not limiting. While the invention is susceptible of various modifications and alternative constructions, it should be understood, that there is no intention to limit the invention to the specific form disclosed, but, on the contrary, the invention is to cover all modifications, alternative constructions, and equivalents falling within the spirit and scope of the invention as defined in the claims.

FIGS. 1-6 show a variety of aspects and embodiments of the present invention. Referring first to FIG. 1a, a diagram depicts one embodiment of the present invention that utilizes microfluidic components. A reservoir 105 containing a volume of liquid-phase sample is connected to a pump 103. The pump drives flow of the sample through tubes 100 toward an aperture 107. The aperture is fabricated in a microfluidic chip 104 in which a channel is formed that connects with the tubing 100 to compose a continuous liquid Slow path that can be returned to the reservoir or can be directed to a waste volume (not illustrated). The liquid-phase sample at the aperture forms a stable liquid-vacuum interface that can be analyzed by a vacuum-based chemical analysis instrument comprising, for example, a detector 101 and a probe beam 102. The instant embodiment further comprises a gas doser 108 directing gas toward the liquid-vacuum interface at the aperture.

Figure 1A:
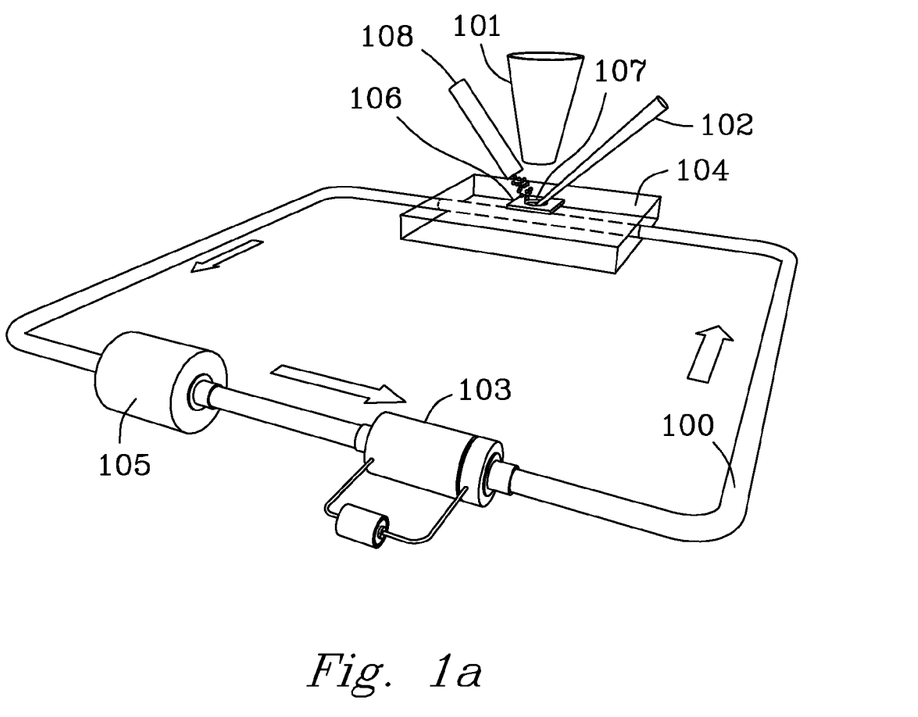
FIG. 1 includes diagrams depicting aspects of one embodiment of a system for analyzing liquids under vacuum.
Figure 1B:
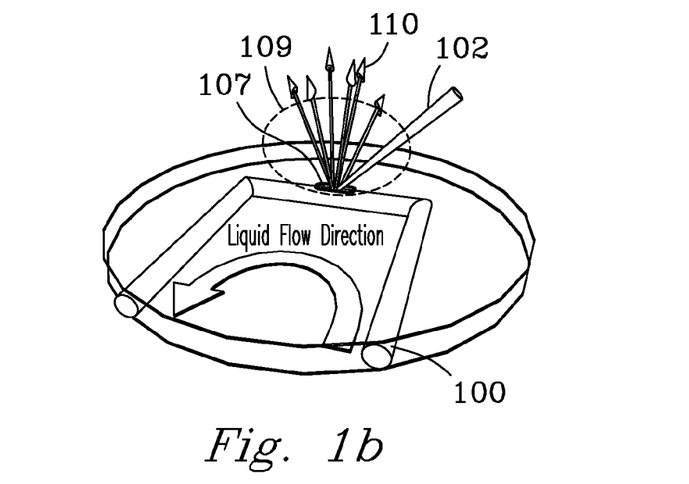

Referring to FIG. 1b, the liquid-phase sample flows through the liquid flow path 100 and past the aperture 107, which can have dimensions on the micrometer scale, exposing a liquid surface directly to the vacuum. The liquid-phase sample does not spray out into the vacuum, but rather forms a stable meniscus held by surface tension against the pressure differences. The region 109 in the vacuum near the liquid can exhibit a relatively higher pressure compared to other regions in the chamber. However, this localized region of high pressure typically only spans a few microns. Probe beams 205 from the vacuum-based chemical analysis installments and emitted species 110 from the liquid surface are able to traverse through it. Furthermore, the gas load is small enough for the analytical devices and the chamber vacuum pumps to tolerate.

Determination of a suitable aperture size for establishing a stable liquid-vacuum interface can be complex since it depends on several variables. The aperture must be large enough to be resolvable by the vacuum-based chemical analysis instruments, yet small enough to limit mean-free path issues. For example, SEM can have nanometer resolution for imaging and about 100 nm resolution for chemical mapping. TOFSIMS can have a resolution of about 130 nm for its Bi beam, and a few microns for its $C_{60}$ beam. These features make it desirable to have an aperture size of at least one micrometer, and several micrometers if using the $C_{60}$ beam.

Furthermore, pressure in the chamber and especially near the aperture must be carefully controlled. The analytical installment probe beam, which can comprise ions, electrons, etc., have to traverse the region above the aperture, where the density of gas can be relatively high due to the evaporation of the liquid-phase sample at the aperture. For example, as a demonstration, assuming that the liquid sample were pure water at room temperature, the liquid surface would be evaporating at a rate consistent with a vapor pressure of water of about 24 Torr. If the system were at equilibrium with an ambient 24 Torr of water vapor, gas molecules would hit the surface at the thermal effusion rate (E). These would add molecules to the surface at a rate of E×S, where S is the "sticking probability" that water molecules strike the surface and become incorporated into it. A reasonable estimate for water sticking probabilities (S) on water is one.

Accordingly, for S=1, the matching evaporation rate must then be equal to $$ES = \rho_0 \sqrt{\frac{kT}{2\pi m}} S$$

where $\rho_0$ is the number density of water molecules at 24 Torr, k the Boltzmann gas constant, T is temperature (Kelvin), and m is the mass per water molecule. Immediately above the surface, the number density of water molecules will be half of the true equilibrium situation at 24 Torr, because the incoming molecules are missing; only evaporating molecules are present. This number density will decrease moving away from the surface, and particularly so for distances (r) larger than the radius (R) of the aperture. The number density can be described according to Eq. (1):

$$\rho(r, \theta) \approx \rho_0 \frac{R^2}{2r^2} H(\theta) \text{ for } r > R, \approx \rho_0/2 \text{ for } r \leq R \quad (1)$$

This $1/r^2$ fall-off is accurate where the molecules are at nearly constant velocity (near the speed of sound). The angular distribution $H(\theta)$ will depend on fundamental desorption angular distributions and the effects of gas-phase collisions upon these. For simplicity here, it is assumed that $H(\theta)$ is constant. A reasonable approximation is to assume that an incoming probe ion or electron must traverse a gas density from about 0 to r of $(\rho_0)/2$, and then traverses a declining pressure following Eq. (1) at further distances. The probability of collision of a gas molecule by the probe particle moving at constant velocity is directly proportional to an integral of this $\rho_0$ times distance dr. The result is that the probe beam needs to essentially traverse a distance of 2R through a pressure of $(\rho_0)/2$, or R through $\mu_0$. For collision effects to be small, R needs to be much less than a mean free path of the probe species at $\rho_0$.

For electron based SEM, the mean free path through a gas for electron energies of 20 keV is millimeters, much longer than the few micrometers characterizing the aperture. The SEM measures electrons exiting the sample. Even at lowest energies of a few eV (secondary electrons), they will easily pass through 24 Torr pressure region spanning only a few microns. The SEM also measures outgoing x-rays produced by the electrons. These too would easily pass through a few microns of 24 Torr gas.

A TOFSIMS instrument commonly uses keV Bi or $C_{60}$ ions as probes, while the detected ions typically start at 0 to 10 eV. Any trajectory that would bring the center of an ion within the packing-distance separation of water molecules, in ice, for example, would likely alter the ion or the water molecule. This corresponds to a distance of 13.5 µm at 24 Torr. For a 3 µm aperture, R is 1.5 µm, making the probability of collision approximately 1.5/13.5 or 0.11. This is an acceptably low number, particularly considering that the incident ions are very heavy, so even a direct collision with single water molecule will not substantially deflect the incident ion or slow it down. It will continue to hit the surface nearly undetected, and certainly change little compared to what will happen when it strikes the aqueous surface approximately one micrometer away. Furthermore, the outgoing ions are not necessarily much heavier than the water molecules. But, considering that this ion has just left an aqueous surface teaming with water molecules. One more encounter with water molecules in the gas phase for 11% of the emitted ions should only result in a minor perturbation.

The pressure rise in the analytical installments cannot be too high. Many instruments are interlocked to shut down if the pressure rises above $10^{-5}$ Torr, for example. Most vacuum analytical instruments have main chamber pumps capable of around 100 L/s pumping speed and tend to have about 30 L of volume. The steady state gas load from a room-temperature, 3 µm-wide aperture into a 100 L/s pumped system will cause a pressure rise of $2.5 \times 10^{-7}$ Torr, which is adequately low. For instruments that require a smaller gas load, a smaller aperture can be employed. Alternatively, the gas load can be reduced by cooling the liquid surface, as described elsewhere herein.

In order to maintain a stable liquid-vacuum interface, the liquid at the aperture needs to be mechanically supported by its surface tension across the opening against the pressure difference inside and outside of the liquid flow path. One way to estimate the parameters required for the establishment of a stable meniscus is to assume that the solution wets the inside of the liquid side of the aperture of radius R and completely does not wet the lip and outer portions of the aperture, then the internal pressure of the liquid will tend to cause the solution to bulge outward above the surface in a partial spherical shape. The area of the spherical cap times the surface tension σ gives the surface energy of the bubble and the derivative of this with respect to the volume of the spherical cap yields the pressure. As in Eq. (2a-2b), this pressure maximizes for y=R at 2σ/R.

$$U = \sigma A = \sigma \pi (R^2 + y^2), \quad V = \frac{\pi y (3R^2 + y^2)}{6} \quad (2a\text{-}2b)$$
$$P = \frac{\partial U}{\partial V} = \frac{4\sigma y}{R^2 + y^2}, \quad P_{max} = \frac{2\sigma}{R}$$

$P_{max}$ is the same as the standard bubble point formula for flow through hydrophobic channels. The result for a for pure water of 0.073 N/m and R of $1.5 \times 10^{-6}$ m is $P_{max}$=97,000 Pa, or just short of 1 bar. Accordingly, under the conditions described above, the surface tension of water can easily hold off the vapor pressure of water (about 0.03 bar), and the pressure needed to push the liquid through the channel (about 0.1-0.2 bar). However, it might not withstand a full bar of pressure. For this reason, it can be important to carefully exclude air bubbles from the system, and use degassed liquids.

The system can comprise either a small aperture for a relatively large static fluid reservoir, or a relatively larger aperture for a flowing liquid. The particular size of the aperture would depend on the physical properties of the liquid sample, the fluid flow path, the vacuum pressure, etc. However, in some embodiments, the aperture is less than 10 micrometers. Preferably, the aperture is between approximately 1 to 5 micrometers.

To minimize drying of the solution due to solvent evaporation, it can be important to maintain a sufficient linear flow rate directly behind the aperture. One way to achieve this is to utilize a narrow liquid flow path. Exemplary widths can less than 30 micrometers. However, at the same time, narrow flow paths can lead to large pressure drops for distances longer than about 30 µm. Accordingly, in one embodiment, the liquid flow path employs two different widths. In a particular implementation, the flow path was about 10 µm wide by 8 µm deep, for a distance of 30 µm near the aperture. The remainder of the liquid flow path can be larger in diameter. The average linear flow rate was 3.5 cm/s (at 208 nL/min fluid flow). The limited length of the narrow section of the flow path prevents the pressure drop from being too high while achieving the desired flow rate.

In some embodiments, an external doser can be employed to balance the evaporation loss of solvent at the liquid-vacuum interface. The net loss of solvent from the interface can result in local cooling of the liquid-phase sample. For prior art devices that employ jets and/or sprays, this cooling can be severe: many tens of degrees of cooling, with eventual freezing of the supercooled liquid. Embodiments of the present invention differ from those systems in that a 10 to 20

μm liquid jet evaporates on all sides, with no thermal anchoring, except via the limited heat capacity of the inside of the jet.

To model the temperature drop precisely would most likely require a full hydrodynamic calculation, as the flow within the liquid flow path should be somewhat parabolic in the flow distribution, until it encounters the hole. Then it should speed near the aperture surface, once the boundary friction is removed. This will alter the contour of the free water interface, and make the actual temperature profile complicated to calculate. However, an approximate determination can be derived much more easily, which is sufficient to guide most designs, For example, using water as an approximation for aqueous samples, as the water surface cools, the evaporation rate drops. The geometry can be approximated using a purely spherical system: instead of a cylindrical aperture with a flat-water interface (or bowed outward by the internal pressure), one can assume that the water is spherical, bowed inward to a hemisphere. Furthermore, it can be assumed that evaporation occurs freely from this entire surface. The radius is chosen so that the hemisphere has the same area as the original disk. This diffusion problem is addressed briefly by Eq. (3) below, and is treated in detail by J. Crank in *The mathematics of diffusion*, Clarendon Press, Oxford, 1979.

$$D\nabla^2 C = \frac{\partial C}{\partial t}; \frac{\partial C}{\partial r} = h(C_1 - C) \text{ at } r = R, \text{ for } h' \equiv h + 1/R; \quad (3)$$

$$\frac{C(r=R) - C_0}{C_1 - C_0} = \frac{hR}{(1+hR)}\left[1 - \exp(h'^2 Dt) * \text{erfc}\left(h'\sqrt{Dt}\right)\right]$$

The expression is given in terms of molecular diffusion for a system initially at condition $C_0$ everywhere. It is suddenly subjected to a change in flux localized at a spherical boundary at r=a, which eventually will lead to a new steady state. This can be applied for estimating the effects of water loss on both concentrations and temperature. For use on temperatures, referring to Eq. (4), C is replaced by T, and D is replaced by κ/c, where κ is the thermal conductivity, c is the volumetric heat capacity, and h becomes $B(T_0)c/\kappa(T_0-T_1)$, where B(T) is the evaporative heat load per unit area. To use this as an estimate, the actual evaporative heat loss versus T is represented with a linearized version, with $T_1$ being the temperature where B extrapolates to zero.

$$\kappa/c\nabla^2 T = \frac{\partial T}{\partial t}; \frac{\partial T}{\partial r} = \left(\frac{B(T_0)c}{\kappa(T_0 - T_1)}\right)(T_1 - T) \text{ at } r = R \quad (4)$$

$$T(r=R) = T_0 + \frac{(T_1 - T_0)hR}{(1+hR)}\left[1 - \exp(h'^2\kappa/c^t) * \text{erfc}\left(h'\sqrt{\kappa/c^t}\right)\right]$$

Figure 2:
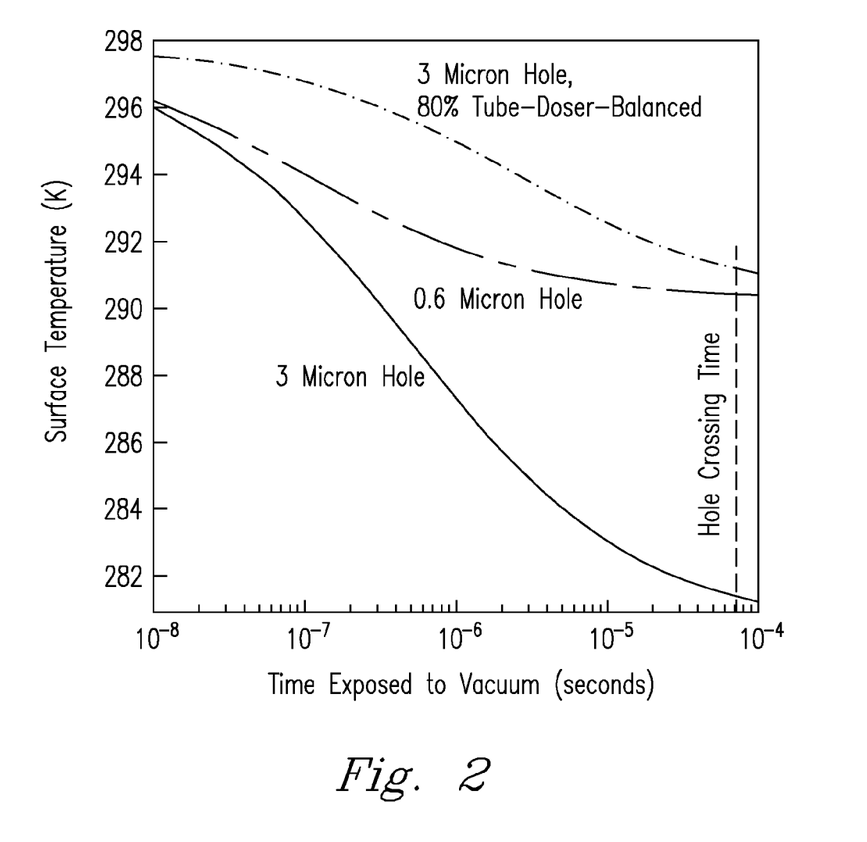
FIG. 2 is a graph of calculated surface temperature as a function of time exposed to vacuum.

FIG. 2 shows the calculated temperature at the surface of the liquid as a function of time from when it first appears in the aperture (assuming plug flow). This is for a 3 μm diameter aperture, channel width/depth of 10 and 8 μm, and flow of 100 μL over 8 hrs. The vapor pressure linearization, with $T_1$ of 272 K, is no worse than about 20% over the range from 298 to 280 K. For these conditions the water reaches the far side of the aperture in about 70 μs, and should cool to about 281.3 K. This is substantial cooling but well above the freezing point. The spherical geometry means that even at infinite time only a limited temperature drop occurs. This asymptotic limit is 281.2K, just slightly lower than calculated by the time the fluid takes to cross the hole, assuming plug flow. So even if the slower flow of the surface of the water is included, the effect would be minor. This cooling is acceptable for many experiments, and even offers some opportunity to study temperature effects. The ratio κ/c is also called the thermal diffusivity. The square root of the aperture crossing time multiplied by this thermal diffusivity give the thermal diffusion distance, which is about 3.1 μm. This being twice the holes 3 μm diameter makes the thermal processes three dimensional, and also makes our calculation quite approximate.

The data in FIG. 2 indicates that decreasing the transit time does not significantly reduce the temperature drop (such as with an order of magnitude increase in the linear flow rate). Cooling can further be decreased by adding an external gas doser to add the evaporated solvent (i.e., water) back. For instance, the temperature drop can theoretically be reduced by a factor of 5 by dosing with 80% of the perfect match (simulating an imperfect doser).

The surface evaporation of the water can change concentrations of solutes. Ignoring cooling, assuming pure water (or dilute solutions) and the temperature is 298 K, the evaporation rate times the hole transit time of 70 μs gives a depth of water loss of 0.23 μm. If the cooling is included, as in the last section, this drops to about 0.08 μm. This is not likely to result in a 0.08 μm depression, as a slight change in trajectories in the flowing water would be all that would be needed to restore the steady-state water-vacuum meniscus. But the solute contained within this 0.08 μm region would have to go somewhere. If the solutes were volatile, they might have evaporated with the water. Non-volatile solutes would be left in the liquid-phase sample. These will diffuse away from the surface. The surface concentration can be calculated with a variation of Eq. (3), where a source of solute is added at the surface, at a rate corresponding to Eq. (5):

$$\frac{\partial C}{\partial r} = \frac{1}{D}\rho_0(T)\sqrt{\frac{kT}{2\pi m}}\frac{1}{\rho_{liq}}(C) \text{ at } r = R \quad (5)$$

where $\rho_0(T)$ is the vapor pressure of water at the time-dependent surface temperature of the water. D is the diffusion constant for the solute. This is in the same form as Eq. (3), except for the temperature dependent vapor pressure and mean speed. Most small ionic solutes, as well as water, have self-diffusion constants falling in the range of 1 to $3\times10^{-5}$ cm²/s. Assuming $1.5\times10^{-5}$ c²/s, the approximate diffusion distance after 70 μs is 0.32 μm. This is small compared to the aperture radius, and 4 times larger than the lost volume of water, i.e., 0.08 μm. To get a simple bracketing estimate, the solution to Eq. (3) is used for the parameters as in Eq. (5), with the vapor pressure and mean speeds fixed at 298 and 281 K. These are the initial and final temperatures calculated in the previous section, for water just appearing in the aperture and just disappearing at the far end. This yields surface concentrations of solute just before it reaches the far side of the aperture of 2.2 and 1.2 times the initial concentration. The best estimate probably lies nearer 1.2 than 2.2, as the vapor pressure drops rapidly with, temperature, and the lower temperature occurs at the exit point. The point of this estimate is to show that the evaporation of water from the aperture is expected to alter the surface concentration of solute, by a modest to large amount. But this is not an indication of catastrophic drying, for solutions well below saturation. The amount of drying can be altered by changing the flow rate.

The pressure inside the system is nominally near vacuum conditions when emplaced in a vacuum chamber and/or analytical instrument. It is possible that when the system is at atmospheric pressure an air bubble might be forced into the liquid flow path, as this pressure difference would exceed the maximum that could be supported by a 3 µm aperture. Once the system was subsequently placed under vacuum, the air might leave through the aperture. However, one could still have a self-supporting interface across the channel. Since the liquid inside the flow system is nearly incompressible, the amount of liquid that could be displaced by the bubble would be small, but still this might occur. To minimize this displacement, some embodiments of the present invention can employ hydrophilic materials and/or surface treatments that increase the hydrophilicity of the liquid flow path.

EXAMPLE

Fabrication of a System Having Microfluidic Components

A polydimethylsiloxane (PDMS) microfluidic device was fabricated using a soft lithography method. First, a template for casting was made on a silicon substrate, with SU-8 photoresist. This made features about 8 µm high using standard photolithography techniques (See FIG. 3A). The microchannel forming a portion of the liquid flow path is 80 µm wide, 2.97 mm long and the narrow part of the channel in the middle is 10 µm wide, 30 µm long. The depth of the whole channel is 8 µm. A 10:1 ratio (w/w) of PDMS prepolymer and curing agent were then thoroughly mixed, degassed under vacuum, poured onto the patterned template to a thickness of 1 cm, and cured in an oven at 75° C. overnight. After removing the patterned PDMS substrate from the template, two 1 mm diameter through-holes were made at the end of the microchannel by punching the substrate with a manually sharpened syringe needle. The channel (i.e., liquid flow path) was enclosed using a silicon nitride (SiN) window (window: 100 nm thickness silicon nitride membrane, 0.5×0.5 mm$^2$; and frame: 200 µm thickness silicon, 7.5×7.5 mm$^2$). The irreversible sealing between PDMS and SiN membrane was generated by oxidizing them both in an oxygen plasma for 1 min and immediately bringing them into conformal contact under a stereomicroscope. The assembly was then placed in an oven at 75° C. for 2 h to form an irreversible bond. Above the channel on the SiN window, a hole 301 serving as the aperture, approximately 2.5 µm in diameter was drilled through the membrane by a focused ion beam (FIB) (See FIG. 3B). Alternately, the aperture can be fabricated by using a TOF-SIMS depth profiling feature as described elsewhere herein.

Figure 3A:
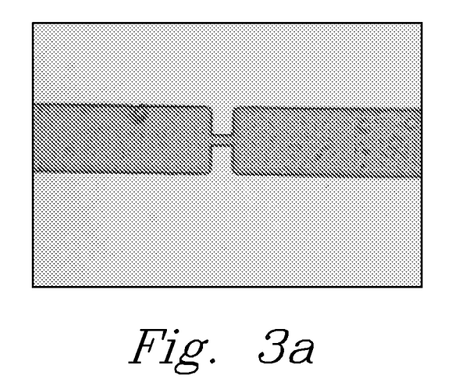
FIG. 3 includes optical micrographs of a (a) microchannel and (b) an aperture in a liquid flow path, as well as a picture of an actual system according to one embodiment of the present invention.
Figure 3B:
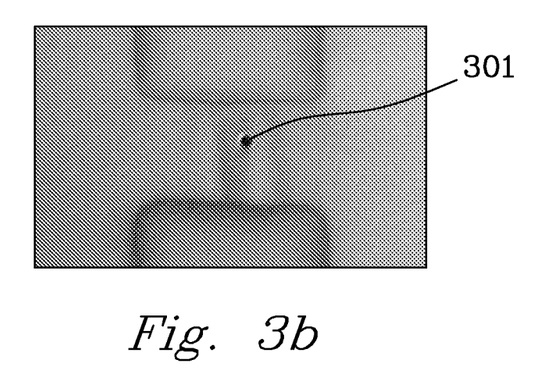
Figure 3C:
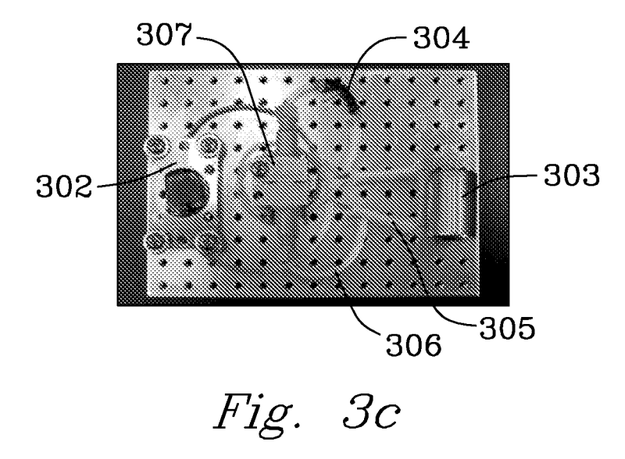

One embodiment of the present invention is shown in FIG. 3C. It comprises a PDMS microfluidic block 302, an electro-osmotic pump 303, a battery 307, and PTFE connecting tubes 306. The PDMS microfluidic block, except for the membrane window was coated by a thin layer of gold film, to reduce gas permeation through the PDMS and to help prevent charging when exposed to the electron or ion beams from any vacuum-based chemical analysis instrument. The continuous flow in the liquid flow path was driven by an electro-osmotic pump, which was powered by a battery. The wire connections were covered by UHV compatible fiberglass sleeving 305. A viton tube 304 was intersected with a short capillary (360 µm OD and 74 µm ID) to form a tee. This tee was initially left open while the various fittings were being connected, to release the extra pressure from trapped dead volumes. The capillary end was then finally closed with an epoxy seal. Without this pressure-relief tee, problems occurred due to the overpressure damaging the SiN film and/or causing fluid to leak out of the aperture.

A dual-beam focused ion beam/scanning electron microscope (FIB/SEM) was used to form the holes in the SiN film. The optical imaging of the channel and the hole was obtained with a microscope. A digital field emission gun environmental scanning electron microscope (ESEM) was used in this work. The microscope could be used in the ESEM mode with up to 10 Torr of water vapor for hydration studies or under high vacuum SEM mode for chemical and morphological studies. The energy dispersed X-ray spectrometer (EDX) utilized a Si(Li) detector with an active area of 30 mm$^2$ and a light element ATW2 window, which allows X-ray detection from elements higher than beryllium (Z>4). The operating vacuum pressure was $2\times10^{-6}$ Torr. A TOFSIMS V spectrometer was used to study the liquid interface. A pulsed 25 keV Bi$^+$ ion beam with an incident angle of 45 degree off the normal was used as the primary ion beam for all measurements. The Bi$^+$ beam was focused into a diameter of about 250 nm and was rastered over a 10×10 µm$^2$ area for imaging acquisition. The focused Bi$^+$ beam was also used to directly drill a hole on the SiN membrane with a circular raster area with a diameter of about 3 µm. The main chamber operating vacuum pressure in these experiments was 1.9 to $4.1\times10^{-7}$ Torr. The interface device is normally preconditioned in a vacuum chamber to check leaks before use of the ESEM or TOFSIMS instruments. The instrument can be easily run on other Bi ions (Bi$_2^+$, Bi$_3^+$, Bi$_3^{2+}$ or Bi$_5^+$), which would give higher sensitivity, but at some expense in beam resolution.

The electro-osmotic pump was adapted for use with the present embodiment. By applying a voltage gradient across a disk of porous glass, water flow is induced. It can produce flows in the 10 µL/min range at 30 V bias, and at reduced flow up to nearly an atmosphere of back pressure. Given the flow and back pressure values associated with the present invention, the pump required only about 3 V bias (at microamps of current). The pump is damaged if the solution being pumped has too much dissolved salt. Accordingly, the salt solution was pumped indirectly, forcing DI water through the pump, to push the solution of interest. To keep the DI water from mixing with the target solution from the parabolic velocity distributions in the reservoir channel, a drop of inert perfluorodecalin liquid was used between the salt solution and the DI water as an immiscible spacer. The surface tension of the water-perfluorodecalin interface is sufficient to provide plug flow at the junction. A similar space is inserted after the DI water. This is because the fluid flow is closed circuit. If the system was inadvertently run too long (>8 hours), this prevents the solution under study from entering the pump, as the particular pump that was utilized does not pump perfluorodecalin. Another liquid performing the same function as perfluorodecalin can be substituted when using other EO pumps.

The pump as-received was designed for use with open-to-air reservoirs and thus was not well configured to insert inline with the instant embodiment. The seal between the electrodes and the polypropylene body leaked in vacuum. To solve these and other problems, an o-ring sealed aluminum box for the pump was made. The box comprised nanoport connectors on each end, and the electrodes were sealed with epoxy, after plasma treating the pump body. The pump was powered using a hermetic, glass-metal-sealed metal-sealed 3.6 V thionyl chloride lithium batteries, suitable for operation under vacuum.

The solutions were routinely degassed to limit pressure build-up inside the system and to prevent bubble formation as discussed earlier. Sometimes this is done by repeatedly boiling the solutions while evacuating them under vacuum using a laboratory setup, then transferring them by syringe to the reservoir. In other cases a commercial degasser was used, which used porous amorphous fluoropolymer membranous tubing and an internal pump.

Of the materials used in the construction, the PTFE tubing and even more so the PDMS, have significant permeability to air and water vapor. This causes several problems, such as permitting air to enter the degassed liquid inside of the PTFE tubes, if it sits too long in air, or raising the pressure in the analytical devices through permeation from within (especially a problem for the PDMS and water). It can even lead to significant changes in solution concentrations and cause memory effects. Another significant issue was the gas load on the chamber. To obtain about a factor of two reduction in ultimate pressure, the PDMS block was sputter-coated with a thin layer of gold. An important step to precondition the interface device was to pre-pump the assembly in the load lock for about an hour, to deplete the water and air in the permeable materials, before loading it into the analytical device. Eliminating the permeable materials will make the interface easier to use. Accordingly, preferred embodiments comprise materials that are non-permeable.

Figure 4A:
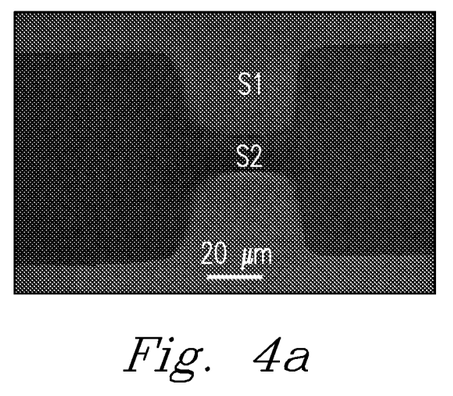
FIG. 4 includes an ESEM image of microchannel (a), an aperture in the microchannel (b), and an EDX spectra at different locations in and near the aperture.
Figure 4B:
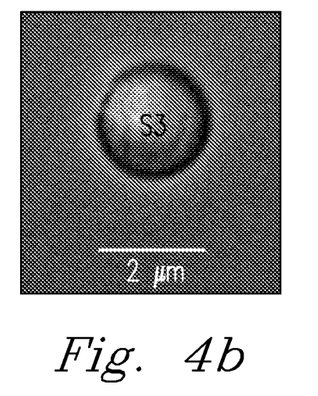
Figure 4C:
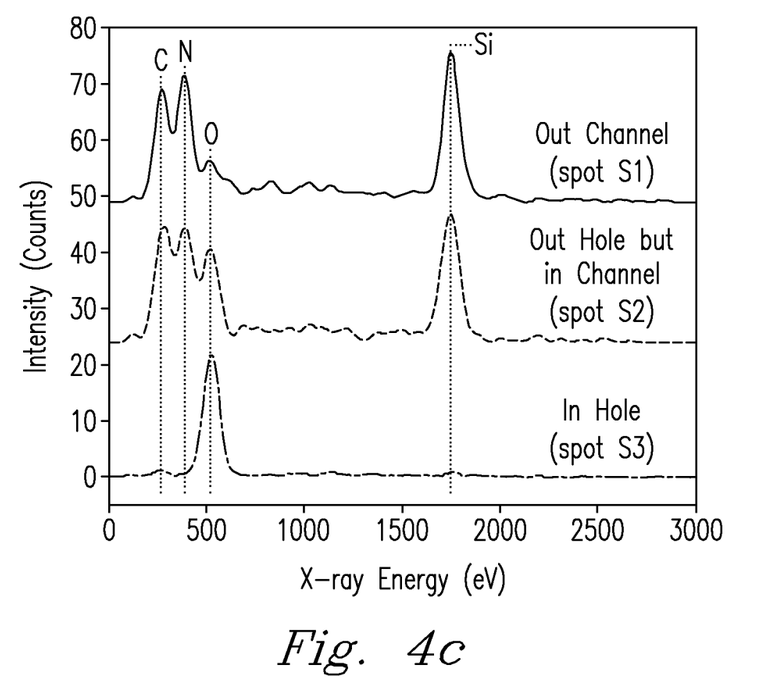

FIG. 4a shows the SEM image of the microchannel filled with DI water. The hole on the membrane window above the microchannel is shown in FIG. 4B, which was taken with a high energy (30 keV) electron beam. The significant contrast in the hole with the edge of the hole indicates the presence of a liquid surface in the hole, which is further confirmed by the EDX results. FIG. 4C shows the intensity of observed elements at different spots, including the spot outside the channel (S1), outside the hole but in the channel (S2) and in the hole (S3), taken at a low energy beam (10 keV). The atomic percentages at the different locations are summarized in Table 1.

TABLE 1

Atomic percent of different spots (S1, S2 and S3 in FIG. 4).

| Location | Atomic Percent (%) | | | | | |
|---|---|---|---|---|---|---|
| | C | O | Si | N | Na | Cl |
| Outside channel (S1) | 38 | 6 | 14 | 41 | 1 | 0 |
| Outside hole but in channel (S2) | 36 | 15 | 12 | 37 | 1 | 0 |
| In hole (S3) | 9 | 86 | 2 | 3 | 0 | 0 |

The low energy beam was chosen for the X-ray data, to reduce the oxygen signals when the SiN film is above the water, since the SiN film nearly blocks the electron beam at that energy. The much higher oxygen atom percent inside the hole demonstrates the presence of the bare water liquid surface compared with the other two locations. Similarly the low atom percent of C, Si and N for the beam over the aperture is also consistent with the bare liquid interface. Holes with no water behind them have also been imaged (not shown). These have very dark secondary electron images, and very weak EDX signals.

Figure 5A:
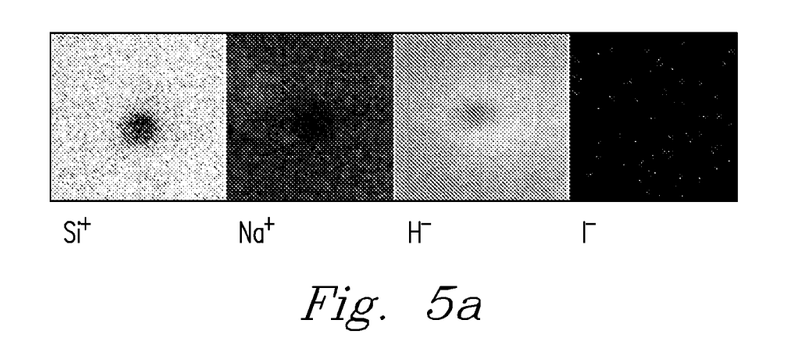

FIG. 5A shows secondary ion images around the aperture, with the channel left unfilled. The beam ion is $Bi^+$, the beam energy is 25 keV, the beam size is about 250 nm. The beam current is about 1.0 pA instantaneously, and it is chopped at 20 kHz, with a beam width of 130 ns. Data shown in FIG. 5A was taken for a total integration time of 65.5 s, over a scan area of 10 μm² square, with 256×256 pixels. A clear hole can be found at the center of the $Si^+$ image with a diameter about ~2 μm, which is consistent with the SEM results. In addition, a low $H^-$ signal is observed in the hole and weak $Na^+$ and $I^-$ signals are observed.

Figure 5B:
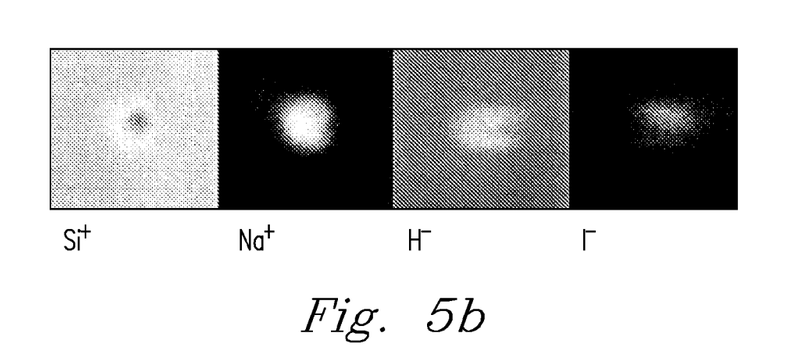

FIG. 5B shows the case of a 0.005 M sodium iodide aqueous solution flowing through the channel. The beam and imaging conditions are the same as that of FIG. 5A. The $Si^+$ image shows the aperture as expected. The $Na^-$ signal has a very bright core, about the same size as the $Si^+$ hole. The $I^-$ signal originates from a region about the size of the $Si^+$ hole. This is compatible with what is expected for imaging the liquid surface. The $H^-$ signal comes from a region a little larger than the hole, as does the less-intense halo of the $Na^+$, which may indicate a small amount of hydrated $Na^+$ adsorbed on the surface of the SiN film. The results show that the aqueous solution is exposed to the vacuum, and its composition can be probed by TOFSIMS.

Figure 5C:
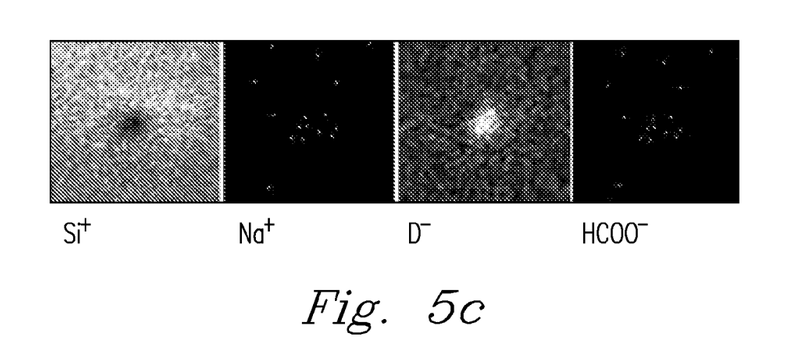
Figure 5D:
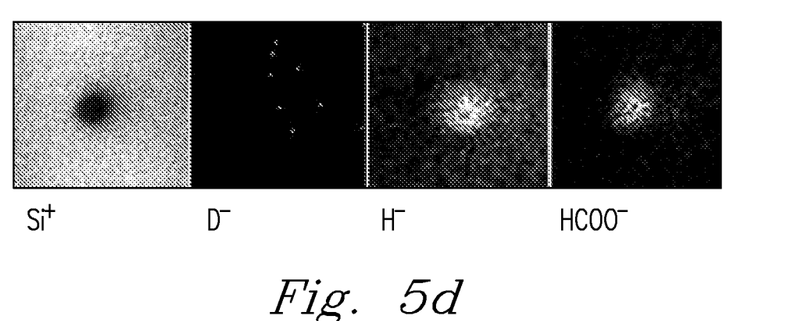
Figure 5E:
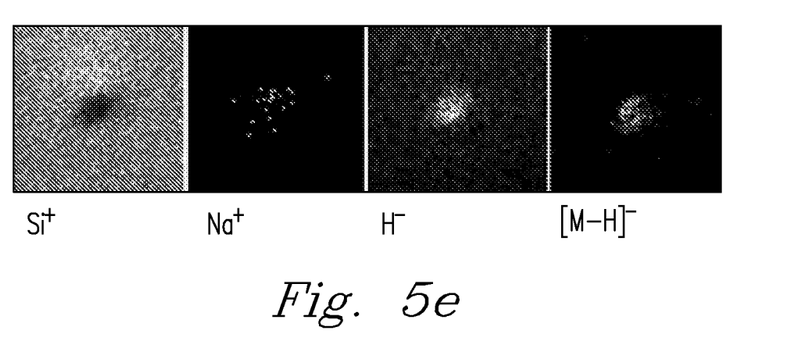
Figure 6:
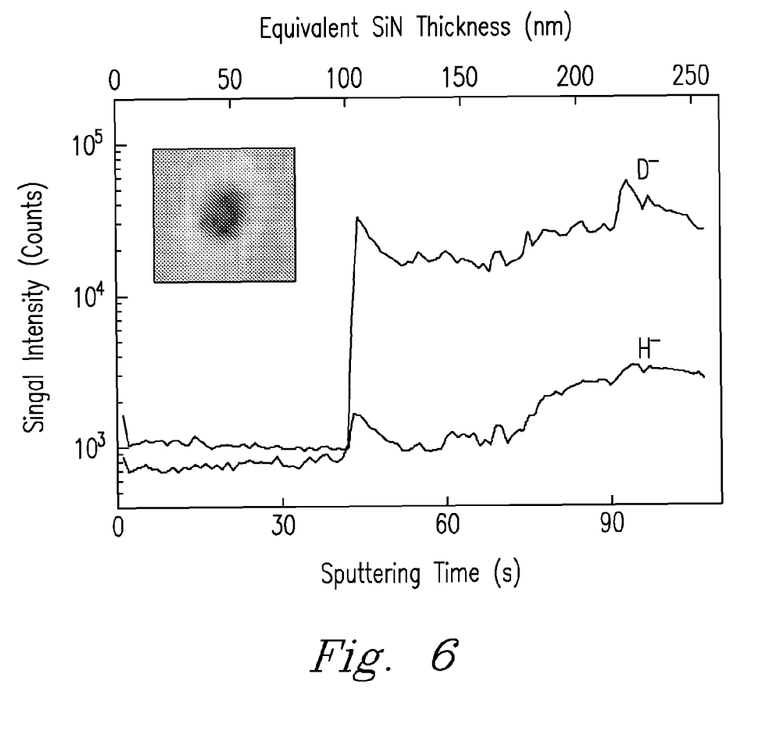
FIG. 6 is a graph of TOFSIMS signal intensity as a function of erosion time when using an ion beam to fabricate an aperture.

The TOFSIMS can also provide an alternative way to make the aperture into the liquid by turning up the beam current. This reduces the handling of the whole device prior to usage and possible contamination, compared to making the hole in advance with the FIB. In one example, the channel contained flowing $D_2O$. The focused 250 nm $Bi^-$ beam was rastered over a circular area with a diameter of 2 μm. To get a rapid sputtering rate, a high average current was required. This was achieved by lengthening the pulse width to 800 ns. The current density is thus about 730 times that used in making the images in FIG. 5. In this mode the mass resolution is very much reduced, so only $H^-$ and $D^-$ could be cleanly separated in SIMS spectra and all other peaks were overlapped due to the very wide pulse. High mass resolution spectra (narrow pulse width) show that $H_2^-$ peak is very weak (<1% of $D^-$), and thus signals around 2.0 amu range can be regarded as pure $D^-$. The TOFSIMS signal was monitored while the intense sputtering was ongoing, yielding a depth profile. The $Bi^+$ beam can drill a hole through the 100 nm silicon nitride layer in about 42 seconds shown in FIG. 6, which includes a graph of $H^-$ and $D^-$ signals vs. $Bi^+$ ion erosion time, while making a hole into the channel by the TOFSIMS using depth profiling. The inset in FIG. 6 is an optical image (10×10 μm²) of the hole.

The $D^-$ signal in the graph shows a dramatic jump (~30 times in signal amplitude) as soon as the $Bi^-$ beam pass through silicon nitride layer, and $H^-$ signal only shows a small jump as low as ~0.8 times. With additional $Bi^+$ dose, a ~50% drop of both $D^-$ and $H^-$ is observed. Then a slow increasing of $H^-$ and $D^-$ signals is observed and the signals seem to get a constant value after ~95 s sputtering. At the initial punch-through, it is likely only a small and irregular hole is formed. The size of the hole becomes larger with additional doses of $Bi^+$ ions. Finally the hole size becomes about 2 μm size, and the $D^-$ and $H^-$ signal become constant. Positive ion spectra (not shown here) show similar behavior.

These data not only validate the feasibility of direct drilling the liquid detection aperture by the $Bi^+$ beam, but also clearly indicate the observation of the liquid surface using TOFSIMS in real-time. FIG. 5C shows the secondary ion images of the resulted aperture. The $Si^+$ image indicates the creation of a hole, and the high $D^-$ signal originates from $D_2O$ flowing in the microchannel. When other liquids are employed, such as 1% formic acid or 0.5% glutamic acid aqueous solutions, the images of the molecular ions [M-H]$^-$ and $H^-$ shown in FIGS. 5D and 5E confirm the results. In addition, the clearer edge of the hole and cleaner background outside the hole shown in FIG. 5C-5E indicate that the in-situ ToF-SIMS depth profiling method for making the aperture can generate less contamination than FIB.

While a number of embodiments of the present invention have been shown and described, it will be apparent to those skilled in the art that many changes and modifications may be made without departing from the invention in its broader aspects. The appended claims, therefore, are intended to cover all such changes and modifications as they fail within the true spirit and scope of the invention.

We claim:

1. A system for analyzing a liquid surface under vacuum comprising a reservoir, a pump, and a liquid flow path, the system characterized by:
   a lack of electrical and fluid connections passing through walls of a chamber having a vacuum pressure in which the system is emplaced;
   the reservoir containing a liquid-phase sample;
   the pump driving flow of the sample from the reservoir, through the liquid flow path, and back to the reservoir, wherein the flow is not substantially driven by a differential between pressures inside and outside of the liquid flow path; and
   an aperture in the liquid flow path exposing a stable surface of the liquid-phase sample to the vacuum pressure within the chamber, the aperture having a radius less than or equal to a critical value required to support a meniscus of the liquid-phase sample by surface tension against the vacuum pressure within the chamber.

2. The system of claim 1, wherein the liquid-phase sample comprises an aqueous or organic solution.

3. The system of claim 1, further comprising at least one vacuum-based chemical analysis instrument to analyze the liquid-phase sample surface region through the aperture.

4. The system of claim 3, wherein the vacuum-based chemical analysis instrument is selected from the group consisting of X-ray photoelectron spectroscopy (XPS), scanning electron microscopy (SEM), secondary ion mass spectrometry (SIMS), helium ion microscopy (HeIM), Auger electron spectroscopy (AES), Rutherford backscattering spectrometry (RBS), and transmission electron microscopy (TEM).

5. The system of claim 1, wherein the vacuum pressure is less than or equal to approximately $5\times10^{-6}$ Torr.

6. The system of claim 1, further comprising a gas doser directing a gas to a region proximal to the aperture.

7. The system of claim 6, wherein the gas comprises a first reactant reacting with a second reactant in the liquid-phase sample.

8. The system of claim 1, wherein surfaces of the liquid flow path, the aperture, or both comprise a surface treatment altering the hydrophilicity.

9. The system of claim 1, wherein the pump comprises an electro-osmotic pump.

10. The system of claim 1, wherein the liquid flow path has a diameter less than 500 micrometers.

11. The system of claim 1, wherein the at least a portion of the liquid flow path has a diameter less than 50 micrometers.

12. A method for analyzing a liquid surface under vacuum, the method comprising the steps of:
   Emplacing a system comprising a reservoir, a pump, and a liquid flow path, in a chamber having a vacuum pressure, the system lacking electrical and fluid connections that pass through walls of the chamber;
   Driving flow of liquid-phase sample from the reservoir, through the liquid flow path, and back to the reservoir, said driving is not substantially provided by a differential between pressures inside and outside of the liquid flow path;
   Exposing a stable surface of the liquid-phase sample through an aperture in the liquid flow path to the vacuum pressure within the chamber, the aperture having a radius less than or equal to a critical value required to support a meniscus of the liquid-phase sample by surface tension against the vacuum pressure within the chamber; and
   Analyzing the liquid-phase sample surface region through the aperture by at least one vacuum-based chemical analysis instrument.

13. The method of claim 12, wherein the vacuum-based chemical analysis instrument is selected from the group consisting of X-ray photoelectron spectroscopy (XPS), scanning electron microscopy (SEM), secondary ion mass spectrometry (SIMS), helium ion microscopy (HeIM), Auger electron spectroscopy (AES), Rutherford backscattering spectrometry (RBS), and transmission electron microscopy (TEM).

14. The method of claim 12, wherein the vacuum pressure is less than or equal to approximately $5\times10^{-6}$ Torr.

15. The method of claim 12, further comprising directing a gas through a gas doser to a region proximal to the aperture.

16. The method of claim 15, further comprising reacting a first reactant in the gas with a second reactant in the liquid-phase sample.

17. The method of claim 12, wherein surfaces of the liquid flow path, the aperture, or both comprise a surface treatment altering the hydrophilicity.

18. A system for analyzing a liquid surface under vacuum comprising a reservoir, a pump, and a liquid flow path, the system characterized by:
   a lack of electrical and fluid connections passing through walls of a chamber having a vacuum pressure less than or equal to approximately $5\times10^{-6}$ Torr in which the system is emplaced;
   the reservoir containing a liquid-phase sample, the liquid-phase sample comprising an aqueous or organic solution;
   the pump driving flow of the sample from the reservoir, through the liquid flow path, and back to the reservoir, wherein the liquid flow path has a diameter less than 500 micrometers and the flow is not substantially driven by a differential between pressures inside and outside of the liquid flow path;
   an aperture in the liquid flow path exposing a stable surface of the liquid-phase sample to the vacuum pressure within the chamber, the aperture having a radius less than or equal to a critical value required to support a meniscus of the liquid-phase sample by surface tension against the vacuum pressure within the chamber; and
   at least one vacuum-based chemical analysis instrument to analyze the liquid-phase sample surface region through the aperture.

19. The system of claim 18, wherein at least a portion of the liquid flow path has a diameter less than 50 micrometers.

* * * * *